Figure 1:
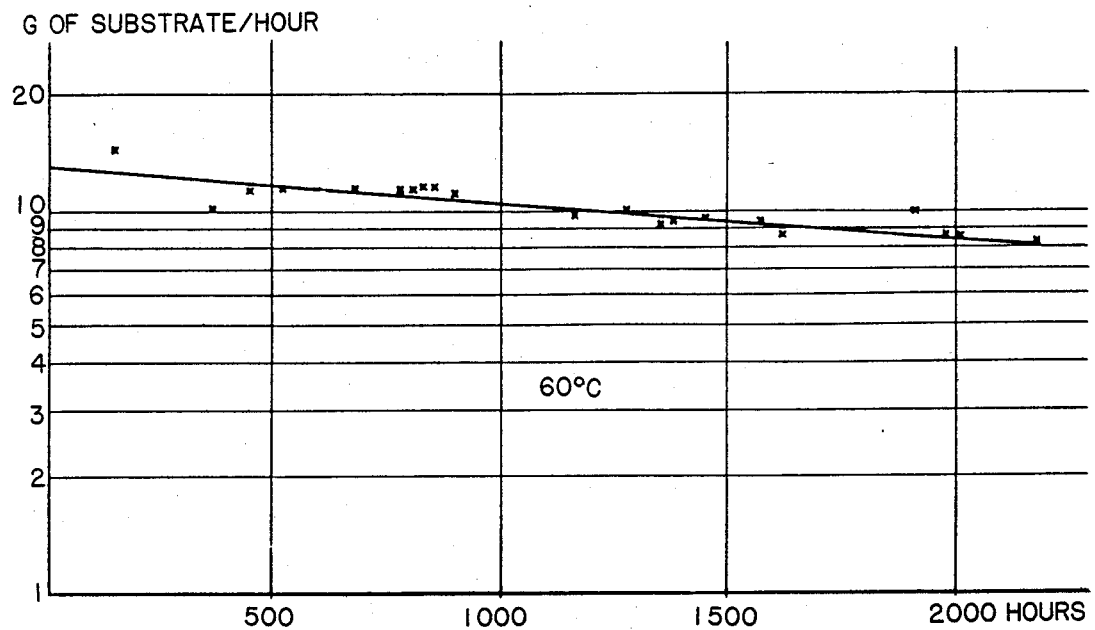

United States Patent [19]

Eigtved

[11] Patent Number: 4,818,695
[45] Date of Patent: Apr. 4, 1989

[54] IMMOBILIZED *MUCOR MIEHE* LIPASE FOR TRANSESTERIFICATION

[75] Inventor: Peter Eigtved, Holte, Denmark

[73] Assignee: Novo Industri A/S, Bagsvaerd, Denmark

[21] Appl. No.: 80,217

[22] Filed: Jul. 31, 1987

Related U.S. Application Data

[63] Continuation of Ser. No. 646,752, Sep. 4, 1984, abandoned.

[30] Foreign Application Priority Data

Sep. 5, 1983 [DK] Denmark .............................. 4025/83

[51] Int. Cl.$^4$ ........................ C12P 7/64; C12N 11/08; C12N 9/20; C12R 1/785
[52] U.S. Cl. .................................... 435/134; 435/180; 435/198; 435/931
[58] Field of Search ................ 435/134, 180, 198, 931

[56] References Cited

U.S. PATENT DOCUMENTS

| | | | |
|---|---|---|---|
| 4,065,580 | 12/1977 | Feldman et al. ................. | 435/198 X |
| 4,078,970 | 3/1978 | Fujita et al. .......................... | 435/180 |
| 4,170,696 | 10/1979 | Hirohara et al. ............... | 435/180 X |
| 4,263,400 | 4/1981 | Ushiro ............................. | 435/180 X |
| 4,275,081 | 6/1981 | Coleman et al. ............... | 435/134 X |
| 4,472,503 | 9/1984 | Matsuo et al. .................. | 435/180 X |

FOREIGN PATENT DOCUMENTS

| | | | |
|---|---|---|---|
| 37667 | 10/1981 | European Pat. Off. ............ | 435/180 |
| 63087 | 4/1982 | Japan .................................... | 435/198 |
| 152886 | 9/1982 | Japan .................................... | 435/180 |

OTHER PUBLICATIONS

"Preparation and Properties of Immobilized Lipases", J. Lavayre et al., Biotech & Bioeng, vol. XXIV, pp. 1007–1013 (1982), John Wiley & Sons, Inc.

"Ester Exchange of Triglyceride by Entrapped Lipase in Organic Solvent", K. Yokozeki et al., Poster, Enz. Eng. 6, Kashikojima, Japan, Sep. 20–25, 1981.

"Application of Immobilized Lipase to Regio-Specific Interesterification of Triglyceride in Organic Solvent", Euro. Journal Appl. Microbial Biotechnol (1982) 14:1–5.

"Application of Immobilized Lipase to Hydrolysis of Triacylglyceride" Y. Kimura et al., Euro. Journal Appl. Microbial Biotechnol. (1983) 17:107–112.

*Primary Examiner*—David M. Naff
*Attorney, Agent, or Firm*—Morris Fidelman; Franklin D. Wolffe

[57] ABSTRACT

Immobilized lipase is produced by mixing an aqueous lipase solution with a particulate, macroporous, weak anion exchange resin, and recovering and drying the resin having lipase immobilized thereon. The resin has a particle size such that more than 90% resin particles have a size between 100–1000 μm. The immobilized lipase is used in a packed bed for continuous transesterification or solvent free fats. Preferably, the lipase is *Mucor miehei* lipase.

9 Claims, 1 Drawing Sheet

IMMOBILIZED *MUCOR MIEHE* LIPASE FOR TRANSESTERIFICATION This application is a continuation of U.S. application Ser. No. 646,752, filed Sept. 4, 1984, now abandoned.

INTRODUCTION

Immobilized lipase preparations adapted for transesterification or interesterification of fats are known. Thus, in U.S. Pat. No. 4,275,081, immobilized lipase preparations are described whereby the lipase is produced by fermentation of species belonging to the genera Rhizopups, Geotrichum or Aspergillus, and whereby the lipase is attached on an inert particular carrier which may be diastomaceous earth or alumina. These carriers exhibit a very high specific surface area. It was believed necessary to use an immobilized lipase preparation with very high specific surface area (i.e., small and porous carrier particles) in order to obtain high enzymatic activity.

Although interesterification can be carried out batchwise without a solvent with such immobilized lipase preparations, continuous interesterification in a column cannot be carried out on an industrial scale without the presence of solvent, (which has to be removed later) because the preparation consists of small particles, which during column operation, generate an unacceptably high pressure drop. It is noteworthy that in European patent application publication No. 069599 wherein an enzymatic rearrangement of fat is described with lipase from Aspergillus species, Rhizopus species, *Mucor javanicus* or *Mucor miehei* supported on a carrier, e.g., Celite, all examples relating to continuous interesterification in a column employ a solvent. An immobilized lipase adapted to column operation interesterification of solvent free fats would be welcomed by the art. However, such a lipase form would not be based upon adsorption of the lipase on a carrier particle, The art has, of course, investigated enzyme immobilized through ionic bonding, covalent binding and entrapment. For example, the inventors of U.S. Pat. No. 4,170,696 note that the controlled size distribution and physical properties of macroporous ion exchange resins offer advantages for enzyme support purposes, These inventors, however, offer objection to the small quantity of enzyme that can be carried per unit weight of the ion exchange resin carrier and suggest employing a diethylaminoethyl (DEAE) derivative of the resins for enzyme support purposes. Teachings such as those posed in U.S. Pat. No. 4,170,696 to the effect that a particular enzyme immobilization technique is broadly applicable to a great many enzyme systems can be criticized for misleading the art. The differences enzyme to enzyme and substrate the substrate make virtually each enzyme/substrate/reaction conditions system an exception to which the broadly applicable technique will apply poorly, if at all.

Lipases, in particular, are exceptional enzymes in that their enzymatic activity functions at the interface of two liquid phases (waterand oil), which alone would indicate that immobilization techniques well suited to other enzymes cannot be expected to apply to lipases well, if at all. The art has recognized that immobilization of lipases present special difficulties. See for example J. Lavaryre et al., "Preparation and Properties of Immobilized Lipases", Biotechnology and Bioengineering, Vol. XXIV, pp. 1107-1013 (1982), John Wiley & Sons. Some workers in the art, did investigate immobilization of lipase by adsorption or ionic bonding, by covalent binding and by entrapment, concluding that adsorption (on celite) followed by entrapment of the celite particles produced by far the best results; see the Poster presented at Enz. Eng. 6, Kashikojima, Japan, Sept. 20-25, 1981 and their corresponding Paper in Eurpoean Journal of Applied Microbiology and biotechnology, No. 14, pp. 1-5 (1982), as well as a successor paper in the same Journal at No. 17, pp. 107-112 (1983).

The prior art referenced hereinabove are but exemplary of the efforts by workers in the art to provide an immobilized lipase suited to facile column operations industrial use. So far as the inventor hereof is aware, all prior art processes adapted for large scale use require solvent; the solvent is used to lower the viscosity of the fatty starting material in order to secure as smooth a column operation as possible. It has hitherto been deemed impossible as a practical matter to avoid solvent in continuous interesterification processes on an industrial scale, due to the high pressure drop in the column, even though significant advantages associated with elimination of solvent from these interesterification processes are quite well known.

Thus, the purpose of the invention is to provide a method for production of an immobilized lipase preparation which will open up the possibility for carrying out the continuous interesterification without a solvent in an economically feasible way.

BRIEF STATEMENT OF THE INVENTION

Now, surprisingly, according to the invention, it has been found that production of an immobilized lipase preparation may be performed very easily by simple mixing of an aqueous solution of lipase and a particulate macroporous weak anion exchange resin and thereafter recovering the resin followed by drying. Then, providing a specified proportion of water content in the final immobilized preparation makes possible conduct of continuous interesterification of fats without a solvent, in an economically feasible way. Water washing the resin after removal of the spent lipase solution is advantageous.

In a preferred embodiment of the method according to the invention a thermostable microbial lipase is employed, desirably a lipase from a thermophilic Mucor species, especially *Mucor miehei*. *Mucor miehei* is a good producer of 1,3-specific lipase, and thus a low cost product can be obtained.

In a preferred embodiment of the method according to the invention more than 90% of the particles of the macroporous weak anion exchange resin has a particle size between approximately 100 and 1000 $\mu$m, preferably between 200 and 400 $\mu$m. In this particle size interval a good compromise between high interesterification unit activity and low column pressure drop is obtained.

In a preferred embodiment of the method according to the invention the proportion between the amount of the aqueous solution of the microbial lipase and the weight of weak anion exchange resin corresponds to 5,000-50,000 LU/g ion exchange resin (dry weight). In this interval, sufficient lipase for commercially available ion exchange resins is provided.

In a preferred embodiment of the method according to the invention when the microbial lipase is derived from a thermophilic Mucor species, especially *Mucor miehei*, the pH during contact between the weak anion exchange resin and aqueous lipase solution is between 5 and 7. A strong bond between the lipase and the ion exchange resin is secured.

In a preferred embodiment of the method according to the invention, the contact time is between 0.5 and 8 hours. In this time interval saturation of the ion exchange resin with lipase is approximated. At least 75% of the lipase activity, preferably more than 80% is removed from the lipase solution.

In a preferred embodiment of the method according to the invention, the separation is performed by filtration; a simple procedure well adaptable to industrial practice.

In a preferred embodiment of the method according to the invention, the separated immobilized lipase is dried to a water content between approximately 2 and 40%, more preferably 5–20% of water. Thereby a final lipase preparation with a high interesterification activity is obtained.

Also, the invention comprises use of the immobilized lipase preparation for a continuous process transesterification or interesterification of fats, wherein melted fat(s), optionally or facultatively mixed with melted or dissolved free fatty acid, is contacted with the immobilized lipase preparations without solvent, at temperatures in the range of 25° C.–85° C., preferably 50° C.–80° C., especially 55° C.–75° C.

DISCUSSION OF THE INVENTION

Thus, the method according to the invention for production of an immobilized lipase preparations intended for interesterification of fats is characterized by the fact that an aqueous solution of a microbial lipase is contacted with a particulate macroporous weak anion exchange resin, namely as ion exchange resin which contains available primary and/or secondary and/or tertiary amino groups. A relatively large average particle size for the resin is employed to make the final product suitable for column operation without excessive pressure drop. The reaction conditions at which the lipase is bonded to the weak anion exchange resin and the reaction time are sufficient to bind the desired amount of lipase to the anion exchange resin, whereafter the thus formed immobilized lipase is separated from the aqueous phase and the separated lipase containing weak anion exchange resin is dried to the desired water content, which preferably is between approximately 2 and 20%. The drying operation can be by vacuum, fluid bed drying or any other drying process suited to large scale operation that does not subject the immobilized lipase to temperature levels at which the lipase becomes deactivated.

It is noted that practice of this invention employs a large average particle size compared to the average particle size of the absorbed lipase product described in U.S. Pat. No. 4,275,081, of which the majority of the particles have a particle size less than about 50 um.

In order not to inactivate the enzyme, prior art interesterification reactions are carried out at the relatively low temperature levels made possible by presence of a solvent capable of dissolving high melting point fats. Surprisingly, it has been found that the immobilized lipase preparations produced according to practice of this invention exhibits sufficient stability is melted fat to catalyze the interesterification, which is to say, at relatively high temperatures. Also, the pressure drop through an interesterification column loaded with the immobilized lipase preparations produced according to practice of this invention is sufficiently low to allow smooth column operation of intersesterification reactions. Also, surprisingly, it has been found that the unique combination of contact conditions, weak anion exchange resin and controlled final water content in the immobilized lipase preparation generates a high specific lipase activity in the melted fat mixture. This result is believed to be in contradistinction to all previous attempts by the art to provide immobilized lipase preparations intended for commercial use without inclusiion of a solvent.

The immobilized lipase preparations produced according to practice of this invention can be prepared with a high enzyme recovery, which result is important to attaining a low cost (continuous) interesterification process.

More than 75% of the lipase activity initially present in the lipase solution may be, and should be removed from the solution by the anion exchange resin. To some extent, the lipase take-up by the resin is time dependent, probably because a significant period of time is required for enzyme molecules to diffuse throughout the macroporous resin particles. A mixing (reaction) time of 8 hours will at least approximate equilibrium saturation of the weak anion exchange resin. Less time, as short as 0.5 hours, produces acceptable results. A reasonable measure for selecting an optimum contact time is removal of lipase activity from the lipase solution. Whatever contact time is required to remove more than 75%, and preferably more than 80% of the lipase activity from the lipase solution may become the reaction time for large scale practice of this invention. It is noted that the available experimental evidence indicates that the optimum contact time will be virtually independent of contact temperature within the range of 5°–35° C., the temperature range of 0°–35° C. is contemplated for practice of this invention.

The physical and chemical differences between various anion exchange resin can, of course, be expected to affect both the immobilization reaction and the immobilized lipase preparation. As might be expected, all of the experimental work done in genesis of this invention involve commercially available macroporous weak anion exchange resins, and practice of this invention was found to be generic to all of the weak anion exchange resins tested. The final immobilized lipase products exhibited a lipase activity of 5,000 to 50,000 LU/gm, (dry basis) with 10,000 to 30,000 LU/gm (dry basis) constituting a preferred range.

The feature of water washing the still wet resin particles separated from the spent lipase solution is particularly advantageous when the available lipase comprises a relatively crude lipase.

Prior art processes of the sort described in U.S. Pat. No. 4,275,081 have required a purified lipase in order to provide usable immobilized lipase preparations. It has, surprisingly, been found that the immobilized lipase preparations produced according to practice of this invention can be prepared directly from a rather crude lipase product. Apparently, impurities that the prior art wished to remove from the lipase do not bond to the weak anion exchange resin and then are removed in the spent lipase solution and/or in the wash water.

All in all, highly advantageous results are obtained from a procedure that, in the ultimate, requires nothing more than mixing a particulate weak anion exchange resin into a rather crude lipase solution of pH 5–7 at room temperature, absent event use of an organic solvent (as is sometimes suggested), then discarding the spent solution and then, desirably, water washing the resin followed by drying the resin to a controlled water content. It is repeated that water washing the separated immobilized enzyme before drying significantly improves the product.

It has been found that the lipase in the immobilized lipase preparations produced according to practice of this invention do not deactivate or remove from the preparations readily, absent adverse pH and/or temperature conditions. Almost no lipase activity appears in the wash water, for example.

Mention has been made that preferred embodiments of this invention are directed to immobilizing thermostable lipses, particularly the *Mucor miehei* lipase. Thermal stability for the lipase is, of course, crucial to interesterification of higher melting point fats, absent solvent. Other advantages also accrue when interesterifying at the highest reasonable elevated temperature level, e.g., reduced likelihood for bacterial contamination and lower fat vicosity.

The temperature range for conduct of intersesterifications according to practice of this invention is 25° C.–85° C., preferably 50° C.–80° C., especially 55° C.–75° C.

Figure 2:
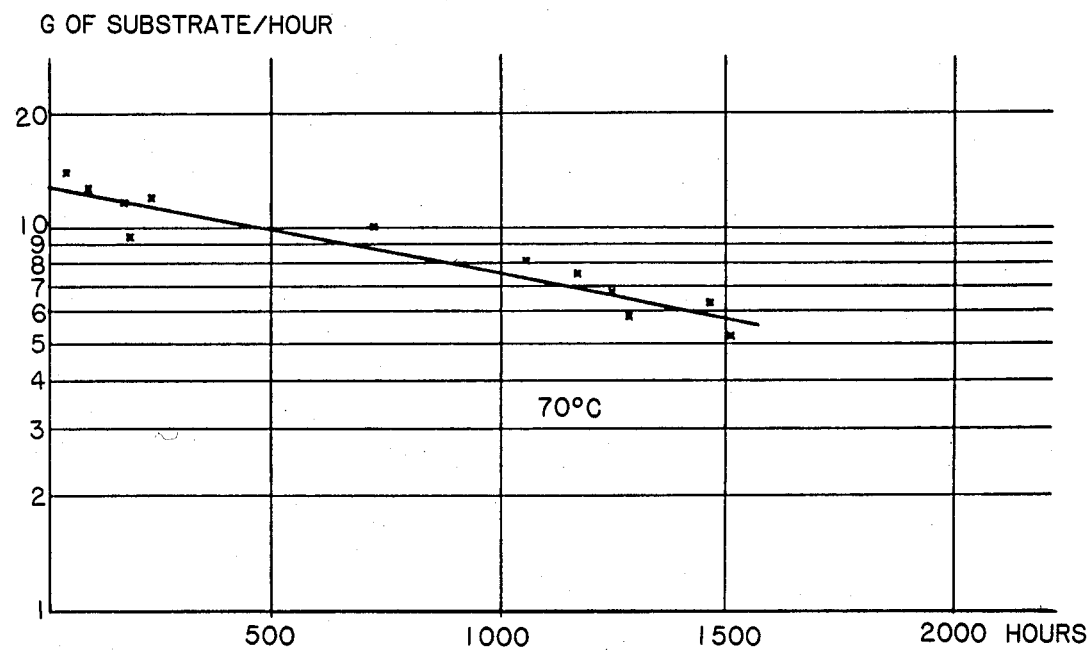

Reference is now made to the attached drawing, whereon is plotted important characteristics of a preferred embodiment immobilized lipase for packed bed (column) continuous interesterification, in which:

FIG. 1 shows the logarithm of the flow rate plotted against time for a run at 60° C.; and FIG. 2 shows the logarithm of the flow rate plotted against time for a run at 70° C.

The lipase activity unit (LU) indicated in the examples hereinafter provided to describe in detail practice of this invention was determined as described in the publication AF 95.1/2-GB of 83-01-03, obtainable from NOVO INDUSTRI A/S, Novo Alle, 2880 Bagsvarerd, Denmark.

The interesterification activity of the immobilized lipase preparations is determined by a batch assay based on the following reactions:

$$OOO + P \rightleftharpoons POO + O$$

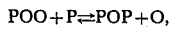
$$POO + P \rightleftharpoons POP + O,$$

where O=oleic acid, P=palmitic acid, and OOO, POO and POP are fats containing the indicated fatty acids in the order indicated, OOO thus being triolein.

250 mg of immobilized lipase preparation is mixed with 600 mg trriolein (0.68 mmol) and 174 mg palmitic acid (0.68 mmol) dissolved in 12 ml petroleum spirit (temp. 80°–100° C.) in a 20 ml glass tube with screw cap. The tubes are incubated in a water bath at 40° C. and shaked for ½, 1 or 3 hours.

The reaction mixture is cooled, filtered and evaporated. The relative amount of OOO, POO and POP is determined by HPLC, and the percentage of incorporated P is calculated as $$\% \text{ incorporated } P = \frac{\% POO + 2 \times \% POP}{3}$$

The equilibrium composition of the above indicated batch reaction mixture is approximately 43% POO and 10% POP or 21% incorporated P.

In some of the following examples the interesterification is carried out as a batch operation with or without solvent. By comparative tests it has been established that an immobilized lipase preparation, which has satisfactory interesterification activity and stability, as demonstrated by the batch interesterification test, and which possesses a particle size distribution and a physical strength suitable for satisfactory column operation, will operate satisfactorily in continuous operation in a column with or without solvent. Thus, a satifactory batch test under these circumstances is evidence that a satisfactory continuous column test can be carried out with the immobilized lipase preparation in question.

EXAMPLE 1

This example illustrates the effect of pH during immobilization of *Mucor miehei* lipase on interesterification activity.

2.0 grams of *Mucor miehei* lipase, 93,000 LU/g, was dissolved in 20 ml of water, and 10 grams of water washed Duolite ES 562 anion exchange resin, dry weight 8.5 g, was suspended herein.

Three such portions were adjusted to pH 5.0, 6.0, and 7.0 respectively and left agitated with magnetic stirring for 4 hours at approximately 5° C.

The three portions were filtered. After filtration the amount of hydrolytic activity (LU) in the three filtrates (before wash) was between 10 and 17% of the total, initial amounts (186,000 LU). Subsequently a water wash was carried out with a small amount of water, and thereafter the preparations were dried overnight in vacuum at room temperature.

The results are summarized in the table below.

| Immobilization pH | Yield g | Water content % | Interesterification activity, 30 minutes | | |
|---|---|---|---|---|---|
| | | | % POO | % POP | % incorporated P |
| 5.0 | 9.20 | 9.5 | 24.5 | 6.2 | 12.3 |
| 6.0 | 9.56 | 8.2 | 26.5 | 6.6 | 13.2 |
| 7.0 | 9.41 | 8.0 | 21.2 | 5.2 | 10.5 |

EXAMPLE 2

Three 10 g portions of moist ion exchange resin, Duolite ES 562 (dry weight 8.35 g) were suspended in 50 ml of water, and 4N NaOH was added until pH stabilized at 6.0 Then they were washed with plenty of water and drained on a Büchner funnel, drained weight approximately 16 g.

To each one of two 10 g portions was added a solution of 2.5 g Mucor miehei lipase (activity 93,000 LU/g) in 25 ml of water, and pH was adjusted to 6.0.

To the third portion was added a solution of 2.5 g of the above indicated *Mucor miehei* lipase in 50 ml of water, and pH was adjusted to 6.0.

The mixture was slowly agitated at room temperature (25°) for 2 hours. Hereafter the liquid was filtered off on a Buchner funnel.

One of the portions with 25 ml lipase solution was furthermore washed with 2×25 ml of water. The immobilized preparations were dried in vacuum.

For the interesterification assay 250 mg (dry weight) of the immobilized lipase preparations were moistened with 20 μl of water prior to mixing with the substrate.

| Lipase preparation immobilized with | Interesterification, ½ hour | | |
|---|---|---|---|
| | % POO | % POP | % incorporated P |
| 2.5 g lipase in 25 ml without wash | 25.8 | 6.85 | 13.2 |
| 2.5 g lipase in 25 ml with wash | 30.1 | 7.65 | 15.1 |
| 2.5 g lipase in 50 ml without wash | 26.8 | 6.86 | 13.5 |

This example demonstrates tht subsequent water wash in order to remove unbound lipase is essential for obtaining a high interesterification activity, whereas the amount of water in which the lipase is dissolved during immobilization, is of minor importance.

EXAMPLE 3

50 g of moist ion exchange resin Duolite ES 562 (dry weight 41.8 g) was adjusted to pH 6.0 and washed as in example 2.

10.6 g portions of this moist ion exchange resin (~5 g dry weight) were mixed with different amounts of a 10% solution of *Mucor miehei* lipase (81,000 LU/g) according to the table.

After the reaction the liquid was filtered off on a Buchner funnel, and the lipase preparation was washed with 2×25 ml water and dried in vacuum to approximately 97% dry matter.

The 250 mg dry weight samples of immobilized preparation for assay purposes were moistened with 20 μl water prior to assaying.

| g of moist ion exchange resin | g of 10% solution of lipase | Reaction time, hours at room temperature | Interesterification, ½ hour | | |
|---|---|---|---|---|---|
| | | | % POO | % POP | % incorporated P |
| 10.6 | 12.5 | 1 | 26.5 | 6.62 | 13.3 |
| 10.6 | 12.5 | 2 | 27.0 | 6.62 | 13.4 |
| 10.6 | 12.5 | 4 | 28.2 | 7.27 | 14.3 |
| 10.6 | 25 | 1 | 23.5 | 5.90 | 11.8 |
| 10.6 | 25 | 2 | 29.7 | 7.56 | 14.9 |
| 10.6 | 25 | 4 | 31.4 | 7.99 | 15.8 |
| 10.6 | 50 | 1 | 19.5 | 4.34 | 9.4 |
| 10.6 | 50 | 4 | 26.6 | 6.73 | 13.4 |

This example shows that the optimal dosage of lipase depends upon the immobilization reaction time.

EXAMPLE 4

Two of the preparations from example 3 were reassayed with varying addition of water, i.e., the sample with 12.5 g lipase solution and that with 25 g lipase solution, both with a reaction time of 2 hours. The effect of the moisture content on the interesterification activity appears from the following table.

| Sample | μl water added to 250 mg dry weight | Estimated moisture in sample % | Interesterification, ½ hour | | |
|---|---|---|---|---|---|
| | | | % POO | % POP | % incorporated P |
| 12.5 g | 0 | 2.6 | 18.2 | 2.27 | 7.6 |
| | 20 | 9.6 | 25.6 | 6.55 | 12.9 |
| | 50 | 18.5 | 23.4 | 5.85 | 11.7 |
| | 100 | 29.9 | 15.3 | 3.84 | 7.6 |
| 25 g | 0 | 3.0 | 19.1 | 2.04 | 7.7 |
| | 20 | 10.0 | 28.6 | 7.65 | 14.6 |
| | 50 | 18.8 | 25.4 | 5.25 | 12.0 |
| | 100 | 30.1 | 18.6 | 4.55 | 9.2 |

This example shows that the optimal moisture content is approximately 10%.

EXAMPLE 5

One of the preparations from example 3 was reassayed with varying amounts of added water. The sample with 25 g lipase solution and 4 hours reaction time was used.

| μl water added to 233 mg dry weight | Estimated water in sample, % | Interesterification, ½ hour | | |
|---|---|---|---|---|
| | | % POO | % POP | % incorporated P |
| 0 | 9.5 | 28.0 | 6.57 | 13.7 |
| 10 | 13.1 | 28.9 | 7.45 | 14.6 |
| 20 | 16.2 | 27.9 | 6.46 | 13.6 |
| 30 | 19.1 | 26.6 | 6.96 | 13.5 |
| 40 | 21.8 | 25.0 | 6.77 | 12.8 |
| 50 | 24.4 | 22.8 | 5.20 | 11.1 |
| 75 | 30.0 | 19.6 | 4.54 | 9.6 |
| 100 | 34.9 | 14.6 | 3.88 | 7.5 |
| 150 | 42.9 | 0.44 | 0 | 0.1 |

EXAMPLE 6

22.8 g of moist ion exchange resin Duolite A 561 (88.2% dry substance) was adjusted to pH 6.0 and washed.

Another 22.8 g sample of Duolite A 561 was crushed partially in a mortar prior to pH adjustment and washing.

To each of these portions were added a solution of 10 g *Mucor miehei* lipase (93,000 LU/g) in 200 g of water adjusted to pH 6. Reaction took place in 2 hours at room temperature.

The immobilized enzymes were washed with 1 liter of water and dried in vacuum.

After drying the uncrushed sample was crushed in a mortar, and both samples sieved.

| Sieve fraction | Interesterification, ½ hour | | | | | |
|---|---|---|---|---|---|---|
| | Crushing prior to immobilization | | | Crushing after immobilization | | |
| | % POO | % POP | % incorp. P | % POO | % POP | % incorp. P |
| 180–300 μm | 30.1 | 7.78 | 15.2 | 25.7 | 6.39 | 12.8 |
| 425–500 μm | 25.7 | 6.66 | 13.0 | 21.7 | 5.50 | 10.9 |
| 600–710 μm | 19.2 | 5.06 | 9.8 | 17.2 | 4.38 | 8.7 |
| 850–1000 μm | 12.7 | 3.22 | 6.4 | 14.3 | 3.90 | 7.4 |

It clearly appears that it is an advantage to use the fine sieve fractions to obtain maximum interesterification activity, but the need for a low column pressure drop makes a compromise necessary.

EXAMPLE 7

This example illustrates the effect of different categories of macroporous weak anion exchange resins (type of matrix, functional groups, particle size) on the batch interesterification activity of the immobilized lipase preparation.

In the case of Duolite ES 562, Duolite A 561, Duolite A 7, Amberlite IRA 93, and Amberlyst A 21 4.25 grams dry weight resin was washed with water, mixed with 1 gram of *Mucor miehei* lipase (93,000 LU/g) in 20 ml of water, the mixture being adjusted to pH 6.0, and rotated slowly for 2 hours at room temperature. After filtration, each preparation was washed with 250 ml of water. In the case of Duolite A 378 8.5 grams was mixed with 2 grams of lipase and finally washed with 250 ml of water. All were dried in vacuum at room temperature. In the case of Duolite A 365, Duolite S 587, and Dowex MWA-1 4.25 gram dry weight resin was mixed with 1 gram of Mucor miehei lipase (124,000 LU/g) in approximately 10 ml of water for 2 hours by rotation at room temperature (in the case of Lewatit, 0.5 of lipase was used, though). After filtration and washing with 2 volumes of water, the preparations were dried in vacuum at room temperature. Characterization of the immobilized preparations is shown in the table below.

ml). The resin was further dried in vacuum to a water content of 10.0%. Yield 8.27 g.

The second third of the wet resin was mixed with a solution of 1 g of the previously indicated lipase in 20 ml of 0.1M sodium acetate buffer (pH 6.0). The pH of the mixture was readjusted to 6 and the mixture was allowed to react for 4 hours at 5° C. with magnetic stirring. During this period the pH dropped to 5.83. The further procedure was carried out as indicated in relation to the first third of the wet ion exchange resin, giving rise to 21 ml filtrate and 9.10 g dried preparation with a moisture content of 9.5%.

The third third of the resin was mixed with lipase solution as before, but pH was kept constant at 6.0 during the 4 hour coupling period at 5° C. by addition of 0.58 ml 1N NaOH. The mixture was worked up as the other thirds, giving rise to 28 ml filtrate and 8.95 g dried preparation with 8.9% moisture. The three filtrates contained between 1 and 5% of the initial, total activity.

The interesterification activity with 250 mg immobilized lipase preparation after a reaction time of 30 minutes at 40° C. is indicated in the following table.

| Anion exchange resin | Matrix | Funct. groups | Partc. sizes, μm (>85%) | Water Batch activity, ½ hour | | | |
|---|---|---|---|---|---|---|---|
| | | | | % | % POO | % POP | % incorp. P |
| Duolite ES 562 | Phenol-formaldehyde | Tert. amine | 212–425 | 13.8 | 26.7 | 6.8 | 13.4 |
| Duolite A 561 | Phenol-formaldehyde | Tert. amine | 300–1200 | 13.0 | 14.8 | 3.2 | 7.1 |
| Duolite A 7 | Phenol-formaldehyde | Second. amine | 300–1200 | 13.5 | 9.5 | 2.5 | 4.8 |
| Duolite A 378 | Polystyrenic | Tert. amine | 300–1100 | 6.3* | 14.3 | 3.3 | 7.0 |
| Amberlite IRA 93 | Styrene-DVB | Poly-amine | 400–500 | 12.2 | 10.8 | 2.9 | 5.5 |
| Amberlyst A 21 | Styrene-DVB | Tert. amine | 425–850 | 11.1 | 10.6 | 2.7 | 5.3 |
| Duolite A 365 | Polystyrenic | Prim. amine | 300–1200 | 11.5 | 15.5 | 3.7 | 7.6 |
| Duolite S 587 | Phenol-form. | Amines | 300–1100 | 7.4 | 25.4 | 6.4 | 12.7 |
| Lewatit MP 62 | Polystyrenic | Amines | 300–1200 | 13.6 | 16.9 | 3.9 | 8.2 |
| DOWEX MWA-1 | Styrene-DVB | Tert. amine | 300–1200 | 10.5 | 21.0 | 4.9 | 10.3 |

*5% water was added before batch assay

EXAMPLE 8

30 g Duolite ion exchange resin type ES 562 was suspended in approximately 75 ml of $H_2O$, and pH was adjusted to 6.0 with 4 N NaOH. The ion exchange resin was washed with water on a suction filter, and excess of water was sucked away. The wet ion exchange resin (approximately 45 g) was divided in three equal portions.

The first third was mixed with a solution of 1 g *Mucor miehei* lipase (210,000 LU/g) in 20 ml of $H_2O$ adjusted to pH 6.0. After mixing the pH was readjusted to 6.0, and the mixture was allowed to react for 4 hours at 5° C. with magnetic stirring. During this period the pH dropped to 5.45. The mixture was transformed to a Buchner funnel with a few milliliters of water and as much as possible of the solution was sucked away (14

| Enzyme preparation immobilized in | Interesterification activity, ½ hour | | |
|---|---|---|---|
| | % POO | % POP | % incorporated P |
| demineralized water, pH 6 | 27.4 | 6.6 | 13.5 |
| 0.1 M acetate, pH 6 | 25.4 | 6.5 | 12.8 |
| demineralized water, pH-stat at pH 6 | 27.7 | 7.0 | 13.9 |

As appears from the table there are only slight differences between the preparations.

EXAMPLE 9

This example illustrates the effects of the presence of two salts in the concentration range 0–0.5M during immobilization on the interesterification activity.

Five 1.00 gram portions of *Mucor miehei* lipase, diafiltrated, and freeze-dried, with an activity of 93,000 LU/g, were dissolved in 20 ml of:

(1) demineralized water
(2) 0.05M sodium phosphate, pH 6.0
(3) 0.5M sodium phosphate, pH 6.0
(4) 0.05M sodium chloride
(5) 0.5M sodium chloride Other five 5.25 gram portions (dry weight 4.25 g) of Duolite ES 562 ion exchange resin were equilibrated with 20 ml of (1)–(5) above. After decantation, the corresponding lipase solutions were added to the wet ion exchange resin particles adjusted to pH 6.0, and the containers were rotated slowly over 2 hours at 25° C. The preparations were then collected by filtration and each washed with 250 ml demineralized water followed by drying in vacuum at 25° C. (64 hours). The results of the interesterification activity assay are shown below:

| Salt/concentration | Yield (g) | % H₂O* | Interesterification activity, ½ hour | | |
|---|---|---|---|---|---|
| | | | % POO | % POP | % incorporated P |
| No salt | 4.51 | 4.7 | 23.1 | 5.7 | 11.5 |
| 0.05 M phosphate | 4.48 | 5.3 | 21.9 | 5.3 | 10.8 |
| 0.5 M — | 4.57 | 4.6 | 20.3 | 5.1 | 10.2 |
| 0.05 M NaCl | 4.54 | 4.6 | 23.4 | 5.7 | 11.6 |
| 0.5 M — | 4.43 | 4.9 | 19.2 | 4.6 | 9.5 |

*additional H₂O up to a total of 10% was added before assay.

EXAMPLE 10

This example shows the effects of high concentrations of sodium acetate during lipase immobilization on the intersesterification activity of the preparations.

Five 1.00 g portions of *Mucor miehei* lipase, diafiltrated and freeze-dried, 93,000 LU/g, were separately dissolved in 20 ml of the following liquids:
(1) demineralized water
(2) 0.5M sodium acetate, pH 6.0
(3) 1.0M sodium acetate, pH 6.0
(4) 2.0M sodium acetate, pH 6.0
(5) 4.0M sodium acetate, pH 6.0

Five 4.25 g (dry weight) portions of Duolite ES 562 ion exchange resin were washed and equilibrated by mixing with the five above indicated solutions (1)–(5) followed by shaking for 15 minutes. Corresponding lipase solutions and washed ion exchange resins were mixed, adjusted to pH 6.0 and rotated slowly for 2 hours at room temperature. Each preparation was filtered, washed with 250 ml of water and dried in vacuum at room temperature. The preparations were assayed for batch interesterification activities, the results being shown in the following table.

LU/g and 4.25 g dry matter of Duolite ES 562 ion exchange resin, washed and pH-adjusted, in 25 ml water at pH 6.0, and by rotation at room temperature for 2 hours. Then washing was performed with 2×25 ml of water, and by vacuum drying 4.93 g of preparation with a water content of 8.1% was obtained.

The activity left in the total filtrate corresponded to 18% of the original activity.

*Aspergillus niger* esterase was obtained by ultrafiltration of the commercial product Palatase from NOVO. 15 ml PALATASE of 2790 LU/ml was immobilized on 4.25 g of ES 562 as described above whereby 4.77 g immobilized preparation with 7.6% water was obtained. The filtrate contained 13% of the original LU-activity.

*Candida cyclindracea* lipse from Amano (type OF) was similarly immobilized by mixing 4.25 g of ES 562 with 1.40 g Amono lipase OF in 15 ml of water, pH 6.0. The yield was 4.62 immobilized preparation with 6.5% of water and 0.2% activity remaining in the filtrate.

The three preparations were characterized as follows:
(1) By the standard batch assay at 40° C.
(2) By a triolein (000)/decanoic acid (D) batch interesterification without solvent at 60° C. using 3.00 g 000, 0.600 g D, and 250 mg dry lipase preparation hydrated to approximately 10% water.

For comparison purposes also results for a *Mucor miehei* lipase preparation, as described in example 13, are listed as well:

| Immobilized lipase | Estim. load LU/mg | 000/P/solvent, 40° | | 000/D, 60° | |
|---|---|---|---|---|---|
| | | Time (h) | % P inc. | Time (h) | % D inc. |
| Fusarium oxysporum | 11 | 3 | 8.0 | 17 | 5.9 |
| Aspergillus niger | 8 | 3 | 4.4 | 17 | 6.5 |
| Candida cylindracea | 30 | 3 | 8.9 | 17 | 1.9 |
| Mucor miehei | 30 | 0.5 | 14.7 | 2 | 13.2 |

| Acetate conc. (M) | Yield after drying (g) | Water after drying (%) | Filtrate | | Batch interesterification activity, ½ hour | | |
|---|---|---|---|---|---|---|---|
| | | | pH | Act. (%)* | % POO | % POP | % incorporated P |
| 0 | 4.81 | 7.8 | 5.2 | 51 | 22.2 | 5.7 | 11.2 |
| 0.5 | 4.67 | 8.0 | 5.8 | 64 | 20.1 | 4.7 | 9.8 |
| 1.0 | 4.72 | 9.6 | 5.8 | 71 | 18.8 | 4.3 | 9.1 |
| 2.0 | 4.73 | 9.1 | 5.8 | 55 | 27.9 | 7.3 | 14.2 |
| 4.0 | 4.75 | 10.4 | 5.6 | 69 | 19.8 | 4.7 | 9.7 |

*Activity in percent of total, initial amount (93,000 LU).

EXAMPLE 11

This example illustrates the immobilization of other microbial lipases than *Mucor miehei* lipase:

*Fusarium oxysporum* lipase, prepared as described in Danish patent application No. 2999/84, Example 23, was immobilized by mixing 6.72 g of lipase of 88,000

In order to assist appreciation of the survey made by the preceding examples, reference is made to the following table.

Exemplary illustration of the influence on the interesterification activity of the immobilized lipase preparations prepared by means of the method according to the invention attributable to:

| Example No. | |
|---|---|
| 1, 8 | pH |
| 2 | subsequent wash |
| 3 | lipase loading in relation to reaction time |
| 4-5 | percentage of water |
| 6 | particle size |
| 7 | type of resin |
| 8-10 | ion strength in lipase solution |
| 11 | microorganism source of lipase |

EXAMPLE 12

This example illustrates continuous interesterification of fats without solvent or other expensive auxiliary agents, using an immobilized lipase preparation prepared according to practice of the invention is a packed bed reactor.

Immobilization 2.20 grams of *Mucor miehei* lipase (81,000 LU/g) was dissolved in 20 ml of water, mixed with 10 grams washed (8.5 g dry weight) Duolite ES 562 ion exchange resin with more than 80% of the particles between 200 and 400 μm. The mixture was adjusted to pH 5.0, and left for 4 hours at 5° C. with magnetic stirring. After filtration and wash with a small amount of water the preparation was dried in vacuum at room temperature. The yield was 9.05 grams, containing 9.3% water. The activity remaining in the filtrate was 8% of the total, initial amount. The batch interesterification activity was 30.6% POO, 7.7% POP at ½ hour or 15.3% incorporated P.

Test in column 2 grams of this immobilized lipase preparation was placed in a column and a solvent-free substrate consisting of olive oil/palmitic acid in the ratio 2.5:1 w/w was continuously fed through at 60° C. The performance of the lipase preparation is shown in the table below.

| Sample/time | Flow gTG/h/ g enz. | Composition (HPLC) OOO % | POO % | POP % | Conversion x, % (GLC) |
|---|---|---|---|---|---|
| Olive oil/start | — | 42.3 | 22.5 | 3.8 | 0 |
| 17 hours | 5.7 | 30.5 | 30.1 | 11.6 | — |
| 208 ½ hours | 2.5 | 33.8 | 28.8 | 8.6 | 28 |
| 233 — | 0.61 | 22.2 | 34.8 | 16.5 | 67 |
| 475 — | 1.8 | 35.1 | 28.8 | 8.7 | 28 |
| Equilibrium (batch) | — | 17.4 | 36.0 | 20.6 | 100 |

Legend: TG: Triglycerides; g enz. = grams of immobilized lipase
% incorporated P is determined by GLC of fatty acid methyl esters
Conversion x = (% P-% $P_0$)/(% $P_{eq}$-% $P_0$). $P_0$, $P_{eq}$ are % incorporated P in the olive oil substrate ($P_0$) and in the TG-mixture at equilibrium ($P_{eq}$).

Comments

Based on the 208½ and 475 hours data, extrapolation to start in semilogarithmic plot indicates an initial activity (flow) of 3.2 g TG/h/g enzyme with a corresponding degree of conversion x=28%. An estimate of the half-life is 500-600 hours at 60° C. without solvent and olive oil/P=2½:1 (w/w). No pressure drop problems have been experienced. An earlier attempt to pass a similar substrate through Celite-adsorbed lipase of the kind described in U.S. Pat. No. 4,275,081 in a column failed.

EXAMPLE 13

This example illustrates a pilot plant scale production of an immobilized lipase preparation adapted for column use and the application of this preparation for continuous interesterification in a column with solvent free substrate at 60° and at 70° C.

Immobilization 6.0 kg (81% dry matter) Duolite ES 562 ion exchange resin was conditioned according to the manufacturer's information (Duolite Technical Information 0110A) by acid-base cycling and in this case also an ethanol rinse (to ensure maximum purity in food processing). The pH was adjusted to 6.0 in 0.1M acetate buffer. The suspension was filled into a column and the settled resin (18 l) was washed with 72 l of water.

18 l of Mucor miehei lipase (10,000 LU/ml) adjusted to pH 6.0 was recirculated at 30 l/h for 6 hours with pH control. After displacement with 20 l of water a combined volume of 37 l contained 126 LU/ml corresponding to 97% immobilization yield. The column was further washed with another 20 l of water and the preparation was vacuum dried at room temperature whereby 6.0 kg (97% dry matter) immobilized lipase preparation was obtained. The batch interesterification activity was 30.2% POO, 6.9% POP at ½ hour or 14.7% $P_{inc}$.

APPLICATION EXPERIMENT NO. 1

4.0 g of the immobilized lipase preparation was filled into a water jacketed column with an internal diameter of 1.5 cm. The temperature in the column was maintained at 60° C. An olive oil/decanoic acid substrate with a composition of 2.5/1 (w/w) was pumped through a precolumn containing 30 g Duolite S 561 saturated with 21 ml of ion exchanged water and further through the main column containing the immobilized lipase preparation. The flow rate was controlled in order to keep the composition of the output at a value corresponding to approximately 65% conversion, i.e. 23% DOO in the final triglyceride (DOO means a triglyceride with one decanoic acid unit in outer position and two oleic acid units).

On the assumption that the decrease of the activity of the immobilized lipase follow a first order reaction the half life can be estimated to 3200 hours. With an initial activity of 2.4 g triglyceride/hour/g enzyme preparation the productivity is appromately 8.3 tons of triglyceride/kg enzyme preparation assuming a run time of two half lives. In FIG. 1 the logarithm to the flow rate is plotted against the time.

APPLICATION EXPERIMENT NO. 2

The same experiment as No. 1 was performed at 70° C. instead of 60° C.

The half life was found to be 1300 hours and the initial activity to 2.3 g triglyceride/hour/g enzyme preparation corresponding to a productivity of 3.2 tons of triglyceride/kg enzyme preparation. The logarithm to the flow rate is plotted against time in FIG. 2.

EXAMPLE 14

This example illustrates the potential of an immobilized lipase preparation produced according to the invention for the continuous interesterification of a high-melting triglyceride mixture composed of beef tallow and soy bean oil without solvent or other auxiliary agents.

Immobilization 19.8 grams of moist (86.0% dry matter) Duolite A 561 ion exchange resin, with more than 80% of the particles between 400 and 850 μm, was adjusted to pH 6.0 in aqueous suspension and washed with water. 50 ml of *Mucor miehei* lipase (7400 LU/ml, 8% dry matter) was mixed with the resin and pH was readjusted to pH 6.0. After stirring for 2 hours at room temperature, filtration and washing with 2×50 ml water, the preparation was dried in vacuum at room temperature. The yield was 19.2 grams containing 8.5% water. The activity left in the filtrate was 34% of the total, initial amount. Batch interesterification activity was 25.4% POO, 6.0% POO at ½ hour or 12.5% inc. P.

Analysis of the interesterification reaction

White beef tallow, and refined soy bean oil were obtained from local markets in Denmark. The substrate was composed of 1.5 parts of beef tallow and 1 part of soy bean oil which were mixed at 70° C. BHT antioxidant was added in a concentration of 0.1%. To characterize the individual components and to follow the interesterification reaction, HPLC was used to analyze the triglyceride composition of the sustrate components, the initial mixture and the interesterified mixture. An initial batch reaction with 2.75 grams immobilized *Mucor miehei* lipase preparation, 24 grams tallow, and 16 grams soy bean oil was run 16.5 hours at 65° C. HPLC showed that the ratio of LPO- to LLL-triglyceride (L: Linoleic, P: Palmitic, O: Oleic) in the mixture increased from 0.62 to 1.16, this latter figure presumably being close to the equilibrium ratio.

Melting properties of the interesterified mixture

The change in melting properties due to interesterification was analyzed by dilatation according to the official IUPAC-method (IUPAC: standard methods for the analysis of oil, fats, and derivatives, 6th ed., method No. 2.141 (1979)). The results appear from the table below, with a corresponding non-interesterified mixture of beef tallow and soy bean oil (1.5:1) as a reference.

|  |  | Temperature, °C. | | | | | | |
|---|---|---|---|---|---|---|---|---|
|  |  | 0 | 20 | 25 | 30 | 35 | 40 | 45 |
| Dilatation (μl/g fat) | Non interesterified mixture | 30.8 | 22.9 | 18.7 | 14.6 | 11.2 | 6.5 | 1.6 |
|  | Interesterified mixture | 16.5 | 4.9 | 4.9 | 3.1 | 0.6 |  |  |

Test in column

A small thermostated column system was operated for 2 days to illustrate a continuous process. 4.0 grams of the described immobilized lipase preparation was placed in a column. Also a pre-column containing 5 grams of moist Duolite A 561 resin (50% dry matter) was used. Beef tallow/soy bean oil in the ratio 1.5:1 w/w was continuously fed through the column system at 67° C. The performance of the immobilized lipase preparation is shown in the table below:

| Sample/time | Flow g TG/h/ g enz. | Composition LPO/LLL | Conversion % |
|---|---|---|---|
| Tallow/SBO - substrate (18 h) | — | 0.65 | ~6 |
| 18 hour's product | 2.10 | 0.90 | 52 |
| 41 hour's product | 1.63 | 0.93 | 54 |
| Equil. (batch) | — | 1.16 | 100 |

I claim:

1. A method for production of an immobilized lipase preparation adapted for interesterification of fats, which comprises contacting an aqueous solution of *Mucor miehei* lipase with a particulate, macroporous, weak anion exchange resin having a particle size such that more than 90% of the resin particles have a size between 100 and 1000 μm, at a pH in range of 5–7 to bind said lipase to said resin to form said immobilized lipase whereby at least 75% of the lipase activity is removed from the aqueous lipase solution to form a spent aqueous solution, then separating the immobilized lipase from the spent aqueous solution and thereafter drying the separated immobilized lipase to a water content of between about 2 and 40%.

2. A method according to claim 1 further comprising water washing the immobilized lipase after separation from the spent lipase solution.

3. A method according to claim 1 wherein more than 90% of the particles of the macroporous weak anion exchange resin has a particle size between about 200 and about 400 μm.

4. A method according to claim 1 wherein the resin is contacted with lipase in solution in an amount of between 5,000 and 50,000 lipase units per gram dry basis ion exchange resin.

5. A method according to claim 1 wherein the lipase solution and ion exchange resin are in contact for between 0.5 and 8 hours.

6. A method according to claim 1 wherein the separated immobilized lipase is dried to a water content between 5 and 20%.

7. The product of the method of claim 1.

8. A method for interesterification of fats which comprises passing solvent free, melted fat(s) through a column of immobilized *Mucor miehei* lipase preparation at a temperature in the range of 50° C.–85° C., said immobilized *Mucor miehei* lipase preparation being a particulate macroporous weak anion exchange resin having particle size such that more than 90% of the resin particles have a size between 100–1000 μm whereon is bound Mucor miehei lipase, said *Mucor miehei* immobilized lipase preparation being of 2–20% water content when starting to pass the melted fat through the column of immobilized lipase.

9. A method according to claim 8 wherein the melted fat contains free fatty acid therein.

* * * * *

Disclaimer

4,818,695.—*Peter Eigtved*, Holte, Denmark. IMMOBILIZED MUCOR MIEHE LIPASE FOR TRANSESTERIFICATION. Patent dated Apr. 4, 1989. Disclaimer filed June 27, 1989, by the assignee, Novo Industri A/S.

The term of this patent subsequent to Jan. 17, 2006, has been disclaimed.
[ *Official Gazette September* 12, 1989 ]

UNITED STATES PATENT AND TRADEMARK OFFICE
CERTIFICATE OF CORRECTION

PATENT NO. : 4,818,695

DATED : April 4, 1989

INVENTOR(S) : Peter Eigtved

It is certified that error appears in the above-identified patent and that said Letters Patent is hereby corrected as shown below:

```
Col. 1, line 39, "particle," should read "particle."
Col. 1, line 61, "waterand" should read "water and"
Col. 1, line 66, "Lavaryre" should read "Lavayre"
Col. 2, line 4, "celite" should read "Celite" (2 occurrences)
Col. 2, line 13, "operations" should read "operations for"
Col. 3, line 30, "preparations" should read "preparation"
Col. 3, line 34, "as" should read "an"
Col. 3, line 56, "um" should read "µm"
Col. 4, line 9, "inclusiion" should read "inclusion"
Col. 4, line 67, "event" should read "even"
Col. 5, line 14, "lipses" should read "lipases"
Col. 5, line 37, "Bagsvarerd" should read "Bagsvaerd"
Col. 5, line 50, "trriolein" should read "triolein"
Col. 6, line 61, "Buchner" should read "Büchner"
Col. 7, line 12, "tht" should read "that"
Col. 7, line 27, "Buchner" should read "Büchner"
Col. 12, line 26, "lipse" should read "lipase"
Col. 12, line 28, "Amono" should read "Amano"
Col. 13, line 25, "is" should read "in"
Col. 15, line 33, "sustrate" should read "substrate"
Col. 15, line 61, "thermostated" should read "thermostatted"
```

Signed and Sealed this

Twenty-third Day of January, 1990

Attest:

JEFFREY M. SAMUELS

*Attesting Officer*   *Acting Commissioner of Patents and Trademarks*